(12) United States Patent
Verdin et al.

(10) Patent No.: US 10,790,524 B2
(45) Date of Patent: Sep. 29, 2020

(54) ELECTROCHEMICAL DEVICE COMPRISING A HYDROGEN SENSOR

(71) Applicant: Commissariat a l'energie atomique et aux energies alternatives, Paris (FR)

(72) Inventors: Baptiste Verdin, Chambery (FR); Remi Vincent, Grenoble (FR)

(73) Assignee: Commissariat a l'energie atomique et aux energies alternatives, Paris (FR)

( * ) Notice: Subject to any disclaimer, the term of this patent is extended or adjusted under 35 U.S.C. 154(b) by 187 days.

(21) Appl. No.: 16/033,658

(22) Filed: Jul. 12, 2018

(65) Prior Publication Data

US 2019/0020044 A1    Jan. 17, 2019

(30) Foreign Application Priority Data

Jul. 12, 2017 (FR) ..................... 17 56603

(51) Int. Cl.
*H01M 8/0444* (2016.01)
*G01N 33/00* (2006.01)
(Continued)

(52) U.S. Cl.
CPC ........... *H01M 8/04447* (2013.01); *C25B 1/08* (2013.01); *C25B 9/066* (2013.01); *C25B 9/20* (2013.01);
(Continued)

(58) Field of Classification Search
CPC ......... H01M 8/04574; H01M 8/04582; H01M 8/0447; H01M 8/0258; H01M 8/0206;
(Continued)

(56) References Cited

U.S. PATENT DOCUMENTS 8,652,698 B2 * 2/2014 Ota .................. H01M 8/04089
429/431
2002/0187075 A1 * 12/2002 Nadanami .......... G01N 27/4074
422/98

(Continued)

FOREIGN PATENT DOCUMENTS

EP    1 293 777 A2    3/2003
EP    1 296 395 A1    3/2003
(Continued)

OTHER PUBLICATIONS

French Preliminary Search Report dated Nov. 29, 2017 in French Application 17 56603 filed on Jul. 12, 2017 (with English Translation of Categories of Cited Documents and Written Opinion).

*Primary Examiner* — Gregg Cantelmo
(74) *Attorney, Agent, or Firm* — Oblon, McClelland, Maier & Neustadt, L.L.P.

(57) ABSTRACT

An electrochemical device includes at least one electrochemical cell, including a membrane electrode assembly and bipolar plates through which at least one discharge manifold passes, the membrane electrode assembly including an active zone and a connection zone; at least one hydrogen sensor including an anode positioned in the connection zone and including a catalyst suitable for ensuring the oxidation of the hydrogen, and a cathode opposite the anode; a voltage source; a current sensor; and a computing unit, suitable for detecting the presence of hydrogen from the measured value of the electric current.

13 Claims, 5 Drawing Sheets

(51) Int. Cl.
*C25B 1/08* (2006.01)
*C25B 9/20* (2006.01)
*G01N 27/407* (2006.01)
*C25B 9/06* (2006.01)
*C25B 15/02* (2006.01)
*H01M 8/0258* (2016.01)
*H01M 8/04537* (2016.01)
*H01M 8/1004* (2016.01)
*H01M 8/0206* (2016.01)
*H01M 8/1018* (2016.01)
*H01M 8/0256* (2016.01)
*H01M 8/0221* (2016.01)
*H01M 8/0228* (2016.01)

(52) U.S. Cl.
CPC .......... *C25B 15/02* (2013.01); *G01N 27/4074* (2013.01); *G01N 33/005* (2013.01); *H01M 8/0258* (2013.01); *H01M 8/04574* (2013.01); *H01M 8/1004* (2013.01); *H01M 8/0206* (2013.01); *H01M 8/0221* (2013.01); *H01M 8/0228* (2013.01); *H01M 8/0256* (2013.01); *H01M 2008/1095* (2013.01)

(58) Field of Classification Search
CPC ............. H01M 8/0221; H01M 8/0228; H01M 8/0256; H01M 8/1004; H01M 2008/1095; G01N 33/005; G01N 27/4065; G01N 27/4071; G01N 27/4047; C25B 1/08; C25B 9/066; C25B 9/20; C25B 15/02
See application file for complete search history.

(56) References Cited

U.S. PATENT DOCUMENTS

| | | |
|---|---|---|
| 2003/0013000 A1 | 1/2003 | Kuroki |
| 2003/0052005 A1 | 3/2003 | Kitanoya et al. |
| 2010/0003549 A1 | 1/2010 | Ota et al. |
| 2017/0279129 A1* | 9/2017 | Vincent .................. G01N 27/42 |

FOREIGN PATENT DOCUMENTS

| | | | | |
|---|---|---|---|---|
| JP | 2002022700 A | * | 1/2002 | |
| WO | WO 2008/032838 A1 | | 3/2008 | |
| WO | WO-2016042257 A1 | * | 3/2016 | .......... H01M 8/0258 |

* cited by examiner

Fig.1

PRIOR ART

ELECTROCHEMICAL DEVICE COMPRISING A HYDROGEN SENSOR

TECHNICAL FIELD

The field of the invention is that of detecting the presence of hydrogen in an electrochemical device comprising a proton-exchange membrane, such as a fuel cell or an electrolyser.

PRIOR ART

Electrochemical devices with an electrolytic proton-exchange membrane, such as a fuel cell or an electrolyser, customarily comprise one or more electrochemical cells each having a membrane electrode assembly (MEA), this being formed of an anode and a cathode separated from one another by the electrolytic membrane.

In the case of an electrolyser, when water is brought to the anode and when a potential difference is applied to the electrodes, the oxidation of the water is carried out, thus producing oxygen and protons. The latter migrate across the electrolytic membrane to the cathode where a reduction of the protons is carried out, thus producing hydrogen. In the case of a fuel cell, the anode carries out the oxidation of the hydrogen introduced, and the cathode produces water by a reduction reaction using the oxygen introduced, and protons and electrons originating from the anode.

However, the electrolytic membrane has a non-zero permeation coefficient with respect to hydrogen, so that hydrogen can diffuse by permeation across the membrane to the opposite electrode. Thus, in the case of the electrolyser, hydrogen can diffuse to the anode and mix with the oxygen produced, which may lead to a risk of ignition when the volume fraction of hydrogen, in the absence of liquid water, becomes greater than around 4%. In the case of a fuel cell, a high proportion of hydrogen at the cathode may result in the presence of a structural degradation of the electrolytic membrane, for example ageing of the membrane or local rupture.

There is therefore a need to detect the presence of hydrogen that has diffused by permeation across the electrolytic proton-exchange membrane in electrochemical devices equipped with such membranes.

Document EP 1 296 395 relates to a fuel cell gasket, positioned on either side of a printed circuit making it possible to extract a measuring signal. In particular, it describes a hydrogen sensor formed of a palladium bridge and an alumina substrate.

Document WO 2008/032838 relates to a fuel cell, one electrochemical cell of which comprises a hydrogen sensor. This is located in a hydrogen distribution channel, downstream of a restriction zone which is an impurity accumulation zone having a reduced hydrogen concentration.

Document EP 1 293 777 describes a hydrogen sensor formed of a membrane electrode assembly.

SUMMARY OF THE INVENTION

The purpose of the invention is to at least partly overcome the drawbacks of the prior art, and more particularly to provide an electrochemical device with an electrolytic proton-exchange membrane comprising a hydrogen sensor.

For this reason, the subject of the invention is an electrochemical device comprising at least one electrochemical cell comprising a membrane electrode assembly formed of an electrolytic proton-exchange membrane, of a first electrode in contact with a first face of the membrane, and of a second electrode in contact with a second, opposite face of the membrane; and two bipolar plates, between which the membrane electrode assembly is located, at least one first discharge manifold passing through said bipolar plates and in fluidic communication with the first face of the membrane; the membrane electrode assembly comprising an active zone delimited by the first and second electrodes, and a connection zone located between the active zone and the first discharge manifold.

According to the invention, the electrochemical device comprises at least one hydrogen sensor, comprising: an anode positioned in the connection zone in contact with the first face and including a catalyst suitable for ensuring the oxidation of the hydrogen, and a cathode in contact with the second face and located opposite the anode; a voltage source suitable for applying a voltage between the anode and the cathode via an electric circuit; a current sensor, connected to the voltage source, suitable for measuring the electric current flowing in the electric circuit; a computing unit, connected to the current sensor, suitable for detecting the presence of hydrogen on the first face from the measured value of the electric current.

Certain preferred but nonlimiting aspects of this electrochemical device are the following.

The computing unit may be suitable for calculating the amount of hydrogen oxidized at the anode from the measured value of the electric current.

The computing unit may be suitable for calculating the amount of hydrogen circulating in the connection zone on the first face, from the measured value of the electric current.

A first bipolar plate may comprise a first fluid distribution circuit in communication with said first discharge manifold and comprising at least one distribution channel superimposed on the anode.

Each bipolar plate may be formed of at least one sheet made of an electrically conductive material.

The anode and the cathode may be electrically insulated from the bipolar plates.

The electrolytic membrane may comprise a protruding portion located in an edge of the connection zone, the voltage source comprising a first conductive track attached to the first face of the membrane and connecting the anode to the protruding portion, and a second conductive track attached to the second face and connecting the cathode to the protruding portion.

The first and second conductive tracks may have a thickness less than or equal to 10 µm.

A first and a second bipolar plate may each be formed of a plate made of an electrically insulating material, and comprising conductive lines arranged so as to polarize, respectively, the first electrode independently of the anode, and the second electrode independently of the cathode.

The first bipolar plate may be made in one piece, and has an inner face and an outer face, the inner face having structurings that form a fluid distribution circuit, the first bipolar plate being suitable for applying a first electric potential to the first electrode and a second electric potential to the anode that is different from the first potential.

The insulating material of the first bipolar plate may define the inner face and the opposite outer face, the inner face comprising fluid distribution channels which are separated longitudinally in twos by a longitudinal wall that comes into contact with the first electrode or with the anode via a bearing surface, electrically conductive lines extending on the bearing surfaces of longitudinal walls and being suitable, for a first set thereof, for applying an electric potential to the first electrode and, for a second set thereof, for applying a different electric potential to the anode.

The first bipolar plate may comprise a first conductive line and a second conductive line, referred to as contact-making lines, extending on the outer face, and first and second conductive vias extending between the outer face and the inner face in the longitudinal walls, the first contact-making conductive line being suitable for applying an electric potential to the first set of conductive lines through conductive vias, and the second contact-making conductive line being suitable for applying a different electric potential to the second set of conductive lines through the other conductive vias.

BRIEF DESCRIPTION OF THE DRAWINGS

Other aspects, objectives, advantages and features of the invention will become more apparent on reading the following detailed description of preferred embodiments thereof, given by way of nonlimiting example, and with reference to the appended drawings in which:

FIGS. 3A to 3E are schematic top views of various parts of an electrochemical device according to a first variant of the embodiment, in which the bipolar plates are of conductive sheet type:

FIGS. 5A and 5B are schematic views of an electrochemical device according to a second variant of the embodiment, in which the bipolar plates are of PCB (printed circuit board) type:

DETAILED DESCRIPTION OF PARTICULAR EMBODIMENTS

In the figures and in the remainder of the description, the same references represent identical or similar elements. Furthermore, the various elements are not represented to scale in order to make the figures clearer. Moreover, the various embodiments and variants are not mutually exclusive and may be combined together. Unless otherwise indicated, the terms "substantially", "around", "of the order of" mean "to within 10%".

Figure 1:
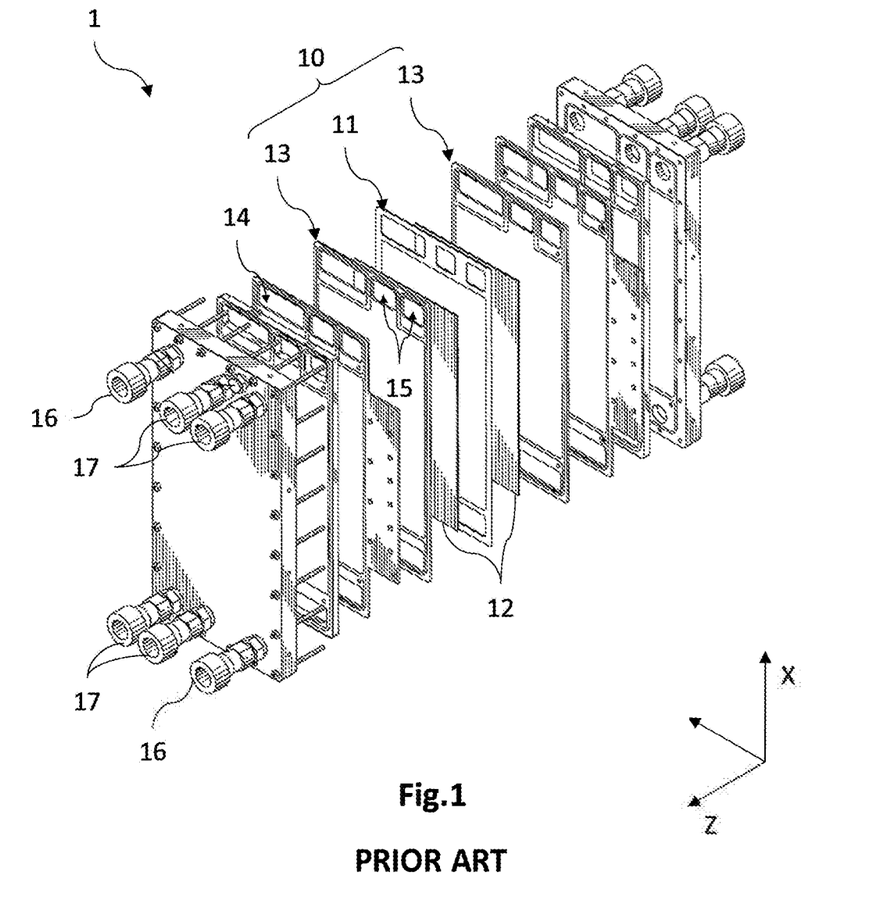
FIG. 1 is an exploded and perspective view of an example of an electrochemical device according to the prior art, comprising a stack of electrochemical cells that each have a membrane electrode assembly (AME)

FIG. 1 illustrates an example of an electrochemical device 1 according to the prior art, here as described in document WO 2004/102710, comprising a stack of electrochemical cells 10 with an electrolytic proton-exchange membrane.

An orthogonal three-dimensional direct coordinate system (X,Y,Z) is defined here and for the remainder of the description where the X and Y axes are oriented along the plane of the electrolytic membrane of each electrochemical cell 10, the X axis being oriented along the main direction of an anodic fluidic flow, and where the Z axis is oriented orthogonal to the plane XY.

Each electrochemical cell 10 comprises a membrane electrode assembly 11 (MEA) formed of a first electrode, for example an anode in the case of an electrolyser, and of a second electrode, for example a cathode, separated from one another by an electrolytic proton-exchange membrane. The anode, the membrane and the cathode are conventional elements known to a person skilled in the art. Each MEA 11 extends along a main plane of the electrolytic membrane parallel to the plane XY. Gas diffusion layers 12 (GDL) here cover the electrodes.

Each MEA 11 is separated from that of the adjacent cells by bipolar plates 13. Each bipolar plate 13 comprises a face intended to be partially in contact with the first electrode of a cell 10, and another opposite face intended to be partially in contact with the second electrode of the adjacent cell 10. Each bipolar plate 13 is suitable for conveying the reactive species to the anode of a first cell 10 on the one hand and to the cathode of an adjacent cell 10 on the other hand, by means of fluid distribution circuits, and for discharging the products resulting from the electrochemical reactions and the non-reactive species through these same distribution circuits, and also for transmitting the electric current between the cells 10. It may also provide, in particular in the case of fuel cells, the flow of a heat transfer fluid between the cells 10 so as to discharge the heat produced.

The electrochemical device 1 also comprises separate flow manifolds 14, 15, each formed of an opening which passes through the stack of cells 10, and more precisely which passes through the bipolar plates 13 facing an edge of the MEA 11. Injection manifolds 14 carry out the injection of reactive fluids from injection ports 16, and discharge manifolds 15 enable the products of the electrochemical reactions to be discharged to the discharge ports 17.

Thus, generally, each electrochemical cell 10 comprises a first distribution circuit connecting a first injection manifold to a first discharge manifold, which is suitable for bringing the incoming reactive fluid $F_{1,in}$ into contact with the first electrode. A second distribution circuit connects a second injection manifold to a second discharge manifold, which is suitable for bringing another incoming reactive fluid $F_{2,in}$ into contact with the second electrode.

Figure 2:
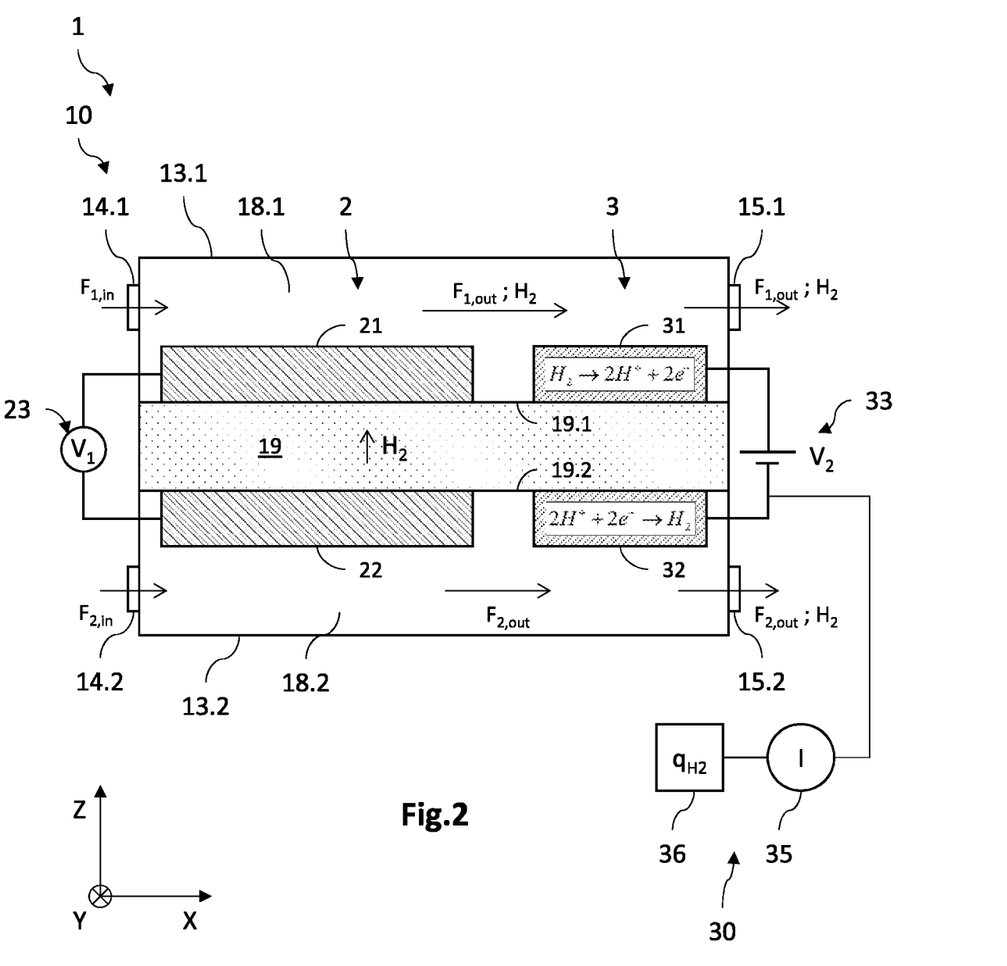
FIG. 2 is a schematic, longitudinal sectional view of an electrochemical device according to one embodiment, comprising a hydrogen sensor having electrodes located in a connection zone of the membrane electrode assembly.

FIG. 2 schematically illustrates, in longitudinal section, an electrochemical device 1 according to one embodiment comprising an electrochemical cell 10 equipped with a hydrogen sensor 30.

The electrochemical cell 10 comprises two bipolar plates 13.1, 13.2 between which an MEA 11 is located. Each bipolar plate 13.1, 13.2 comprises a fluid distribution circuit 18.1, 18.2 suitable for ensuring the flow of a fluid at an electrode 21, 22 of the MEA 11 between two flow manifolds, more precisely between an injection manifold 14.1, 14.2 and a discharge manifold 15.1, 15.2. The distribution circuit 18.1, 18.2 is formed of a network of distribution channels that extend between an inlet communicating with the injection manifold 14.1, 14.2 and an outlet communicating with the discharge manifold 15.1, 15.2. The first bipolar plate 13.1 makes it possible to convey a reactive fluid to a first electrode 21 of the MEA 11, and the second bipolar plate 13.2 enables the flow of another fluid to and/or from the second electrode 22.

The membrane electrode assembly 11 comprises a same electrolytic proton-exchange membrane 19 separating, on the one hand, the first electrode 21 from the second electrode 22 which are located opposite one another and, on other hand, an anode 31 from a cathode 32 of the detection sensor 30 which are located opposite one another.

The first and second electrodes 21, 22 delimit the active zone 2 of the MEA 11. Therefore, the MEA 11 comprises the active zone 2 and also a so-called connection zone 3, the latter being located between the active zone 2 and a discharge manifold 15.1, and more precisely between the active zone 2 and the first discharge manifold 15.1. Thus, the electrolytic membrane 19 is coated with first and second electrodes 21, 22 in the active zone 2 only and not in the connection zone 3. In the active zone 2 electrochemical reactions take place that contribute to the electrochemical efficiency of the device 1: the active zone 2 is thus the site of the electrolysis of water in the case of an electrolyser, and the site of the generation of water by reaction of hydrogen and oxygen in the case of a fuel cell. Therefore, the connection zone 3 may be said to be inactive in the sense that it does not contribute to the electrochemical efficiency of the device.

The electrolytic membrane 19 enables the diffusion of protons from an anode to a cathode, the anode and the cathode being located opposite one another, it being possible for the protons to be within the membrane in the form of $H_3O^+$ ions. It has a non-zero hydrogen permeation coefficient, thus allowing the diffusion of hydrogen across the membrane from the cathode to the anode. The electrolytic membrane 19 is monolithic, and is made of the same material over its entire surface area. It may thus be made from materials customarily chosen by a person skilled in the art, such as those marketed under the reference Nafion 115 or Nafion 117 in the case of an electrolyser which has a hydrogen permeation coefficient of the order of $1.25 \times 10^{-4}$ cm$^3$/s/cm$^2$ at 80° C. and at atmospheric pressure, or those marketed under the reference Nafion 211 in the case of a fuel cell.

The first electrode 21 is in contact with the first face 19.1 of the electrolytic membrane 19 and receives a reactive fluid $F_{1,in}$ through the first distribution circuit 18.1, namely oxygen in the case of a fuel cell or water in the case of an electrolyser. It comprises an active layer suitable for carrying out a reaction for oxidation or reduction of the incoming fluid $F_{1,in}$, the active layer having a catalyst that promotes this electrochemical reaction.

The second electrode 22 is in contact with the second, opposite face 19.2 of the electrolytic membrane 19, and receives hydrogen to be oxidized in the case of a fuel cell, or generates hydrogen in the case of an electrolyser. It comprises an active layer suitable for carrying out a reduction or oxidation reaction, the active layer having a catalyst that promotes this electrochemical reaction.

The first and second electrodes 21, 22 are electrically connected to one another by an electric circuit 23 which allows electrons to circulate between the two electrodes 21, 22 and enables, in the case of an electrolyser, the application of an electric potential difference between the first and second electrodes 21, 22. In this case, the applied voltage V1 is positive, in the sense that the electric potential set at the first electrode 21 is greater than that set at the second electrode 22. It may be between 1.3 V and 3 V, for example equal to around 1.8 V, for a current density between, for example, 50 mA/cm$^2$ and 4 A/cm$^2$. In the case of a fuel cell, the electric circuit 23 may comprise an electric charge, at the terminals of which an electric potential difference is applied by the electrodes 21, 22.

In the case of a fuel cell, the first electrode 21 is a cathode that carries out a reduction reaction producing water from oxygen introduced, and protons and electrons originating from the second electrode 22. And the second electrode 22 is an anode that carries out a reaction for oxidation of the hydrogen introduced. Due to the permeation of the electrolytic membrane 19, hydrogen can diffuse from the second face 19.2 to the the first face 19.1 of the electrolytic membrane 19, and flow into the first cathode distribution circuit 18.1.

In the case of an electrolyser, the first electrode 21 is an anode that carries out a reaction for oxidation of the water introduced, and the second electrode 22 is a cathode that carries out the reduction of the protons. Due to the permeation of the electrolytic membrane 19, hydrogen can also diffuse from the second face 19.2 to the first face 19.1, and flow into the first distribution circuit 18.1.

The hydrogen sensor 30 comprises a detection anode 31 and a detection cathode 32, both located in the connection zone 3, between the active zone 2 and the discharge manifold 15.1, downstream of the first electrode 21 in the longitudinal direction of fluid flow from the injection manifold 14.1 to the discharge manifold 15.1. The hydrogen sensor 30 is suitable for detecting the presence of hydrogen in the first distribution circuit 18.1 by oxidation of at least one portion of the hydrogen present. The anode 31 and the cathode 32 are separated from one another by the same electrolytic membrane 19, and the sensor 30 further comprises a voltage source 33 that makes it possible to apply a potential difference V2 between the anode 31 and the cathode 32.

The detection anode 31 is in contact with the first face 19.1 of the electrolytic membrane 19 and is located in the connection zone 3 of the MEA 11 so that it is accessible by the fluid $F_{1,out}$ flowing in the first distribution circuit 18.1. It is separate from the first electrode 21 in the sense that it is electrically insulated therefrom. It comprises an active layer suitable for carrying out the oxidation of the hydrogen, this layer comprising a catalyst that promotes this oxidation reaction, for example platinum particles supported by carbon, or even palladium. The reaction for oxidation of the hydrogen is written:

$$H_2 \rightarrow 2H^+ + 2e^-$$

The detection cathode 32 is in contact with the second face 19.2 of the electrolytic membrane 19 and is opposite the detection anode 31, while being in fluidic communication with the second distribution circuit 18.2. It is separate from the second electrode 22 in the sense that it is electrically insulated therefrom. It comprises an active layer suitable for carrying out the reduction of the protons that have diffused across the electrolytic membrane 19 with the electrons resulting from the oxidation of the hydrogen. The active layer comprises a catalyst that promotes this reduction reaction, for example platinum particles supported by carbon, or even palladium. The reaction for reduction of the protons is written:

$$2H^+ + 2e^- \rightarrow H_2$$

The hydrogen sensor 30 comprises an electric voltage source 33 that makes it possible to apply an electric potential difference V2, preferably a DC potential difference, between the detection anode 31 and the detection cathode 32, thus enabling the oxidation of at least one portion of the hydrogen present at the anode 31, the circulation of the electrons to the cathode 32, then the reduction of the protons at the cathode 32. By way of example, the applied voltage V2 is of the same sign as the electric potential difference between the electrodes 21, 22 in the case of an electrolyser or a fuel cell. Generally, it has a lower value, as an absolute value, than the voltage V1 and may be equal to around 0.2 V, or even to around 0.4 V. The voltage source 33 thus comprises a voltage generator associated with an electric circuit formed of conductive tracks connecting the voltage generator to the anode 31 and to the cathode 32.

The hydrogen sensor 30 comprises an electric current sensor 35, connected to the voltage source 33. The current sensor 35 measures the value of the current optionally circulating in the electric circuit of the voltage source 33, depending on whether hydrogen, optionally initially present in the first distribution circuit 18.1 is oxidized at the anode 31.

The hydrogen sensor 30 also comprises a computing unit 36, connected to the current sensor 35, which is suitable for detecting the presence of hydrogen on the first face 19.1 of the electrolytic membrane 19, i.e. in the first distribution circuit 18.1. From the measured value of the electric current, the computing unit 36 may be able to calculate the amount of hydrogen oxidized at the anode 31. Advantageously, the computing unit 36 incorporates a database (nomogram obtained previously) or an electrochemical model that makes it possible to estimate, from the measured value of the electric current, the amount of hydrogen circulating in the connection zone 3 on the first face 19.1 of the electrolytic membrane 19, i.e. in the first distribution circuit 18.1. The database may have been obtained previously, for example by connecting, for one point of the polarization curve of the electrochemical cell 10, the amount of hydrogen circulating in the first distribution circuit 18.1 as a function of the value of the electric current provided by the sensor 35.

Thus, the electrochemical device 1 comprises a hydrogen sensor 30 incorporated within the electrochemical cell 20, in the sense that it makes it possible to detect the possible presence of hydrogen in the first distribution circuit 18.1, i.e. on the side 19.1 of the electrolytic membrane 19 where hydrogen is capable of having diffused by permeation.

The hydrogen sensor 30 thus makes it possible to detect, in real time, the presence of hydrogen that has diffused by permeation across the electrolytic membrane 19, or even to provide the amount of hydrogen oxidized at the detection anode 31. It advantageously makes it possible to estimate the amount of hydrogen circulating in the first distribution circuit 18.1, at the outlet of the active zone 2. Thus, this information can be used in order to limit the risks of ignition in the case of an electrolyser and/or in order to know the state of health of the electrolytic membrane 19 (degree of ageing, local rupture, etc.).

Thus the need to resort to specific instrumentation of the electrochemical cell 20, which may be difficult or expensive to use, is avoided. The hydrogen sensor 30 further has the advantage of reducing the volume proportion of hydrogen in the outgoing fluid $F_{1,out}$ which circulates in the first distribution circuit 18.1, by the very fact of detecting the hydrogen present by oxidation.

The operation of the electrochemical device 1 is now described in case of an electrolyser.

Water $F_{1,in}$ is injected at the inlet of the first distribution circuit 18.1 through the injection manifold 14.1, and comes into contact with the first electrode 21, which here is an anode. In this example, water $F_{2,in}$ may also be injected at the inlet of the second distribution circuit 18.2 through the second injection manifold 14.2. The water is oxidized at the first electrode 21 of the active zone 2, which generates oxygen that circulates in the first distribution circuit 18.1, and the protons are reduced at the second electrode 22, thus generating hydrogen that circulates in the second distribution circuit 18.2.

However, hydrogen generated at the second electrode 22 diffuses by permeation across the electrolytic membrane 19 to the first electrode 21. At the outlet of the active zone 2, the fluid $F_{1,out}$ circulating in the first distribution circuit 18.1 thus comprises oxygen and also a non-zero volume proportion of hydrogen.

The outgoing fluid $F_{1,out}$ then passes through the connection zone 3, located between the active zone 2 and the first discharge manifold 15.1. It thus comes into contact with the detection anode 31, which then carries out the oxidation of at least one portion of the hydrogen present, a non-zero voltage V2 being applied between the electrodes 31, 32. The protons then diffuse to the cathode 32 and the electrons circulate in the electric circuit of the voltage source 33. The reduction of the protons is then carried out at the cathode 32.

The current sensor 35 thus measures a non-zero value of the electric current flowing in the voltage source 33, and the computing unit 36 detects the presence of hydrogen when the measured value is not zero. The unit 36 may also calculate the amount of hydrogen that has been oxidized at the anode 31. The computing unit 36 may further estimate the amount of hydrogen circulating in the first distribution circuit 18.1 at the outlet of the active zone 2 from the measured value of the electric current.

FIGS. 3A to 3E illustrate, as a top view, various parts of the electrochemical device 1 according to a first variant of the embodiment.

In this variant, the bipolar plates 13 are formed of sheets made of an electrically conductive material, the distribution circuits 18 of which may be obtained by stamping or moulding. They thus allow electrical circulation between the first and second electrodes 21, 22. The detection anode 31 and the detection cathode 32 are then electrically insulated from the bipolar plates 13 but are in fluidic communication with the distribution circuits 18 of the latter.

Figure 3A:
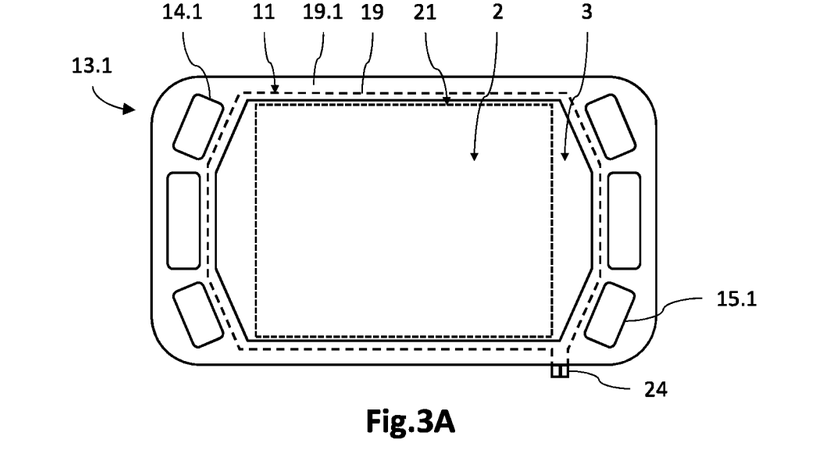
FIG. 3A illustrates a bipolar plate covering an MEA.

FIG. 3A is a top view of a first bipolar plate 13.1 in fluidic communication with the first face 19.1 of the electrolytic membrane 19. In this example it comprises three injection manifolds: a first manifold 14.1 for the incoming fluid $F_{1,in}$ intended to come into contact with the first electrode 21, a second manifold for the incoming fluid $F_{2,in}$ intended to come into contact with the second electrode, and here a third manifold for injecting a heat transfer fluid intended to circulate in a cooling circuit, in the case of a fuel cell. It further comprises three discharge manifolds: a first manifold 15.1 for receiving the outgoing fluid $F_{1,out}$ circulating in the first distribution circuit 18.1, a second manifold for receiving the fluid $F_{2,out}$ circulating in the second distribution circuit, and a third manifold for the heat transfer fluid. The active zone 2 of the MEA 11 is illustrated by dotted lines, as is the electrolytic membrane 19. Thus, the connection zone 3 of the MEA 11 is located between the active zone 2 and the first discharge manifold 15.1. As described in detail subsequently, the electrolytic membrane 19 comprises a protruding portion 24 which sticks out from the contour of the bipolar plate 13.1.

Figure 3B:
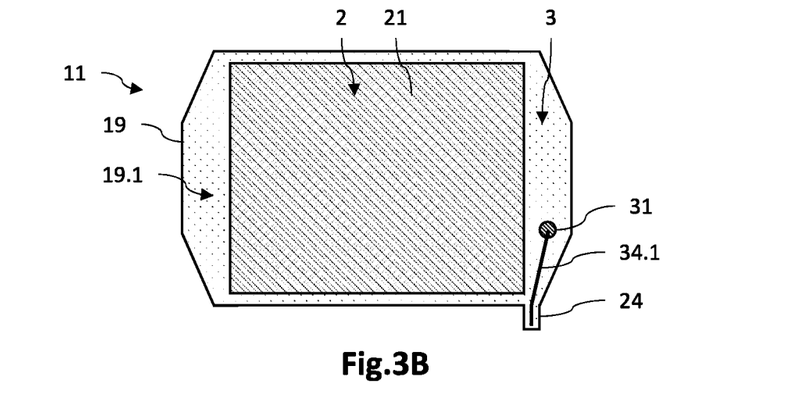
FIGS. 3B and 3C illustrate an MEA, on the side of the first electrode (FIG. 3B) and on the side of the second electrode (FIG. 3C), the membrane of which comprises a protrusion, into which a conductive track in contact with the detection anode or cathode extends.
Figure 3C:
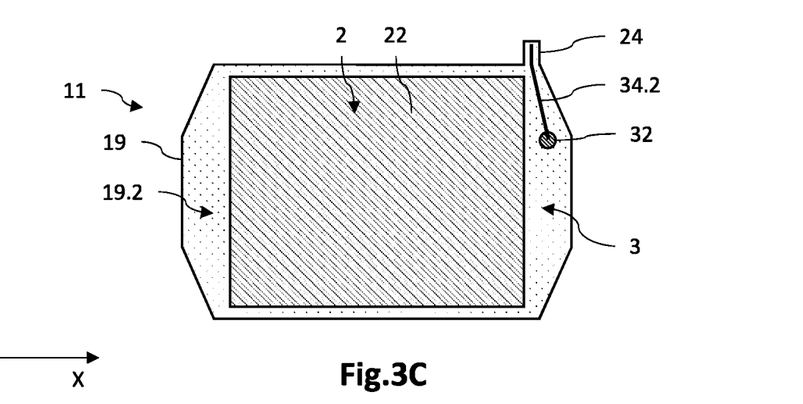

FIGS. 3B and 3C are top views of an MEA 11, on the side of the first electrode 21 for FIG. 3B and on the side of the second electrode 22 for FIG. 3C. The anode 31 is in contact with the first face 19.1 of the electrolytic membrane 19 and is positioned in the connection zone 3, and the cathode 32 is in contact with the second face 19.2 and opposite the anode 31. The anode 31 and the cathode 32 are separate, and therefore are electrically insulated, respectively, from the first electrode 21 and from the second electrode 22.

The electrolytic membrane 19 comprises a protruding portion 24 located at an edge of the connection zone 3. The protruding portion 24 has a size such that it juts out beyond the contour of the bipolar plates 13, and is therefore accessible from the outside of the stack of electrochemical cells.

The current source comprises a first conductive track 34.1 which extends continuously on the first face 19.1 from the anode 31 with which it is in electrical contact to the protruding portion 24. It comprises a second conductive track 34.2 which extends continuously on the second face 19.2 from the cathode 32 with which it is in electrical contact to the protruding portion 24. The conductive tracks 34.1, 34.2 may take the form of a printed circuit board, for example produced by deposition of an ink formed of a conductive material and of an ionomer, advantageously having a thickness less than or equal to 10 μm. Thus, local overthicknesses, which may induce sealing defects or inhomogeneities of mechanical stresses, are limited. Thus, the voltage generator may be easily connected to the conductive tracks 34.1, 34.2 in so far as they stick out from the contour of the bipolar plates.

Figure 3D:
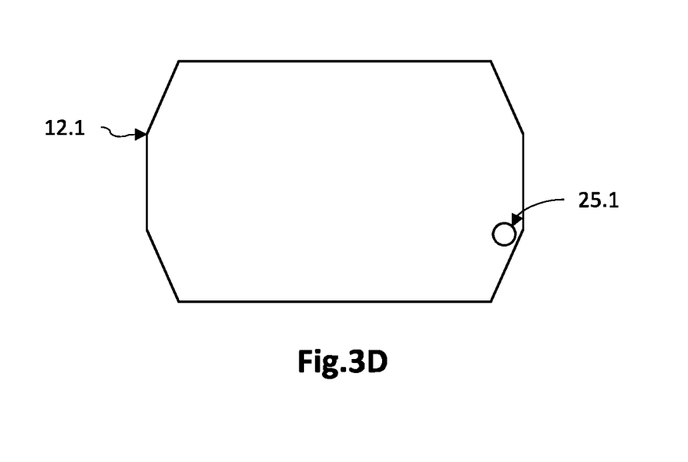
FIGS. 3D and 3E illustrate a diffusion layer having a through-aperture (FIG. 3D), this diffusion layer covering the first electrode of the active zone, so that the through-aperture is positioned opposite the detection anode (FIG. 3E)
Figure 3E:
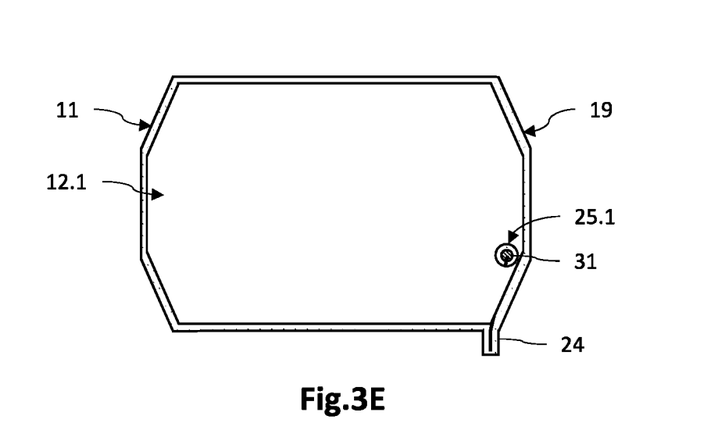

FIGS. 3D and 3E are top views of a diffusion layer 12.1 (GDL, for gas diffusion layer) comprising a through-aperture 25.1. The first diffusion layer 12.1 is intended to come into contact with the first face 19.1, and to cover the active zone 2 and the connection zone 3. To prevent the diffusion layer 12.1 from coming into contact with the detection anode 31, a through-aperture 25.1 is provided, the contour of which is sized to prevent any contact with the edge of the anode 31. Thus, electrical contact between the diffusion layer 12.1 and the anode 31 is avoided while allowing the outgoing fluid $F_{1,out}$ to reach the latter. The same applies for a second diffusion layer with respect to the cathode. The conductive tracks are also electrically insulated from the diffusion layers, for example by an insulating film (not represented) forming a reinforcement of the MEA.

Preferably, an electrically insulating but porous polymer film (not represented) may be positioned between the anode 31 and the first bipolar plate 13.1. The film may be a polymer such as marketed by the company Celgard, for example Celgard 2500. Thus, the electrical insulation between the anode 31 and the first bipolar plate 13.1 is increased, while preserving the fluidic communication between the first distribution circuit 18.1 and the anode 31. The same applies for the cathode 32 with respect to the second bipolar plate 18.2.

Figure 4:
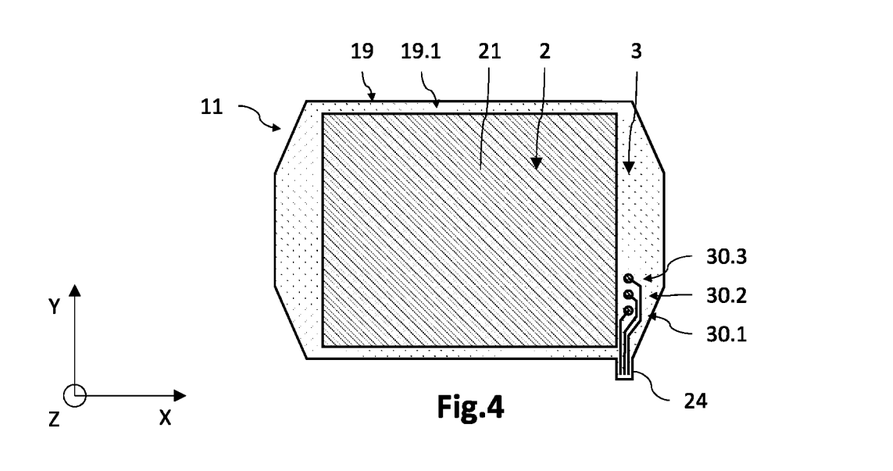
FIG. 4 is a schematic top view of the MEA according to another variant of the embodiment, comprising a plurality of hydrogen sensors positioned at the outlet of one or more fluid distribution channels.

FIG. 4 illustrates a top view of an MEA according to another variant, on the side of the first electrode 21, which differs from that of FIG. 3B essentially in that the device 1 comprises a plurality of hydrogen sensors 30.1, 30.2, 30.3. Each hydrogen sensor 30.1, 30.2, 30.3 comprises an anode and a cathode positioned in the connection zone 3. The detection anodes of the various hydrogen sensors 30.1, 30.2, 30.3 are electrically insulated from one another and are each placed opposite one or more channels of the first distribution circuit. The detection cathodes are located opposite the corresponding anodes. The hydrogen sensors 30.1, 30.2, 30.3 comprise first and second conductive tracks, which extend to a protruding portion 24 of the electrolytic membrane 19. Several protruding portions may be provided, or a single protruding portion as represented here. Thus, it is possible to detect the presence of hydrogen in a localized manner, and thus to indicate if one or more distribution channels comprise more hydrogen than the others. This makes it possible in particular to carry out a more precise monitoring of the state of health of the electrolytic membrane 19, and to more precisely locate a possible rupture of the membrane. Microvalves may be provided, for the purpose of closing the distribution channels where the rupture of the membrane would be located.

Figure 5A:
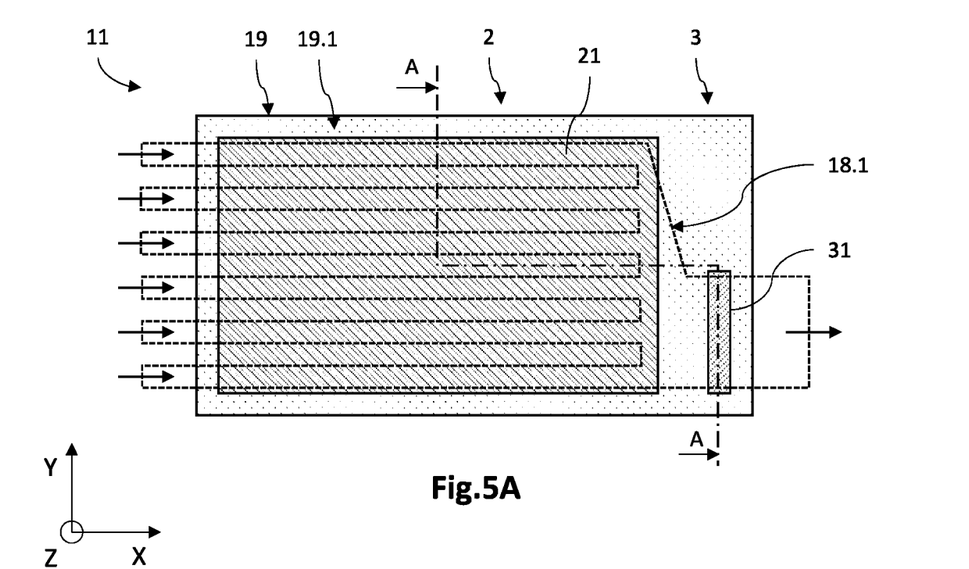
FIG. 5A illustrates, as a top view, on the side of the first electrode, an MEA covered by distribution channels.
Figure 5B:
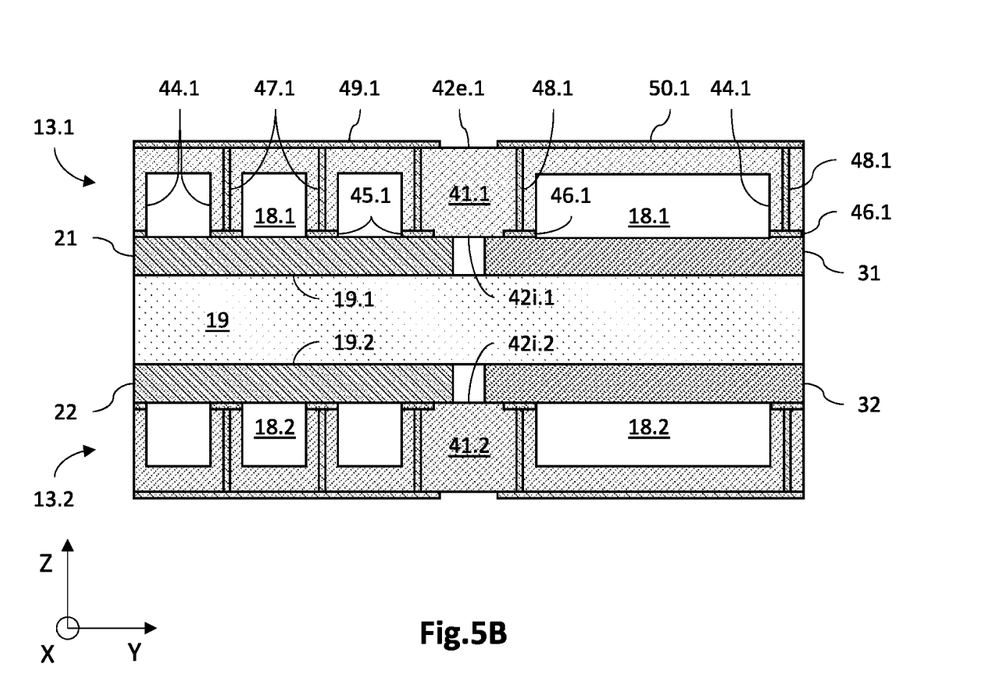
FIG. 5B illustrates a portion of the electrochemical device in cross section along the plane A-A illustrated in FIG. 5A.

FIGS. 5A and 5B illustrate, as a top view (FIG. 5A) and in cross section (FIG. 5B), various parts of the electrochemical device 1 according to a second variant of the embodiment.

In this variant, the bipolar plates 13 comprise a structured plate made of an electrically insulating material within which conductive lines extend that are suitable for polarizing the first and second electrodes 21, 22 independently of the detection anode 31 and detection cathode 32. Thus, the detection anode 31 and the detection cathode 32 are then in contact with the insulating material of the bipolar plates 13 but are electrically insulated from the first and second electrodes 21, 22. The bipolar plates 13 are then of PCB printed circuit board type.

FIG. 5A is a top view of an MEA 11 on the side of the first face 19.1 of the electrolytic membrane 19, and of an example of a first distribution circuit 18.1 illustrated by dotted lines.

The MEA 11 thus comprises an electrolytic membrane 19, the first face 19.1 of which is coated by the first electrode 21 which delimits the active zone 2, and by the detection anode 31 located in the connection zone 3. A plurality of distribution channels crosses the active zone 2 and, here purely by way of illustration, meet in the connection zone 3 in order to form a flow homogenization zone. Other arrangements of the channels are of course possible. Thus, as examples, the distribution channels may remain separate from one another in the connection zone, or even meet in groups.

Unlike the first variant, in so far as the polarization of the detection anode 31 and of the detection cathode 32 is carried out by the bipolar plates 13, the electrolytic membrane 19 does not comprise a protruding portion that receives conductive tracks of the current source.

FIG. 5B illustrates, schematically and partially, in cross section along the cutting plane A-A illustrated in FIG. 5A, an example of bipolar plates 13 of PCB type according to this second variant.

Illustrated here is the MEA 11, of which a first zone forms the active zone 2 and a second zone, separate from the first, forms the connection zone 3, located downstream of the active zone 2 in the fluidic continuity of the first distribution circuit 18.1, in the direction of the first discharge manifold 15.1 (not represented). The active zone 2 comprises the first electrode 21 and the second electrode 22 which are separated from one another by the electrolytic membrane 19, and the connection zone 3 comprises the anode 31 and the cathode 32 which are separated from one another by the same electrolytic membrane 19. The anode 31 and the first electrode 21 are separate from one another in order to avoid any electrical contact, in the same way as the cathode 32 and the second electrode 32 are. In a known manner, the electrolytic membrane 19 conducts protons but is insulating with respect to electrons.

The distribution circuits 18.1, 18.2 are formed by structuring the bipolar plates. Thus, the first distribution circuit 18.1 is made in a same bipolar plate 13.1 having structurings that define fluid distribution channels, which bipolar plate is suitable for applying an electric potential to the first electrode 21 and another different electric potential to the anode 31. Likewise, the second distribution circuit 18.2 is made in a same bipolar plate 13.2 having structurings that define fluid distribution channels, which bipolar plate is suitable for applying an electric potential to the second electrode 22 and another, optionally different, electric potential to the cathode 32.

In this example, each bipolar plate 13.1, 13.2 is of PCB (printed circuit board) type. It thus comprises a portion 41.1, 41.2 made of an electrically insulating material, for example a ceramic on and in which electrical lines extend.

With reference to the first bipolar plate 13.1 (the second bipolar plate 13.2 is identical here), the insulating portion 41.1 has an outer face 42e.1 and an inner face 42i.1 opposite one another along the thickness axis of the plate 13.1. The inner face 42i.1 is oriented towards the first face 19.1 of the electrolytic membrane 19, and comprises structurings that define the distribution circuit 18.1.

The channels of the distribution circuit 18.1 are separated in twos and bordered by a longitudinal wall 44.1 of the insulating plate 41.1, the end of which, forming a bearing surface in contact with the first electrode 21 or with the anode 31, is at least partially coated by an electrical track 45.1, 46.1 referred to as a polarization track.

Thus, all or part of the ends of the longitudinal walls 44.1 separating and bordering the distribution channels is coated with such an electrical polarization track 45.1, 46.1. The polarization tracks 45.1 contact the first electrode 21, and the polarization tracks 46.1 contact the anode 31. The polarization tracks 45.1 are electrically insulated from the polarization tracks 46.1.

The polarization tracks 45.1, in contact with the first electrode 21, are connected to an electrical track 49.1 referred to as a contact-making track which extends on the outer face 42e.1. The contact-making track 49.1 is connected to the polarization tracks 45.1 by first vias 47.1. The vias 47.1 are through-apertures filled with an electrically conductive material, which extend along the thickness axis of the insulating plate 13.1 in the longitudinal walls 44.1.

Similarly, the polarization tracks 46.1, in contact with the detection anode 31, are connected to another contact-making electrical track 50.1 that extends on the same outer face 42e.1. The contact-making track 50.1 is connected to the polarization tracks 46.1 by vias 48.1. The first and second contact-making electrical tracks 49.1, 50.1 are electrically separated from one another.

Thus, the same bipolar plate 13.1 forms a first fluid distribution circuit 18.1 for the first electrode 21 and the detection anode 31, and makes it possible to apply mutually different electrical potentials to these two electrodes 21, 31.

The second bipolar plate 13.2 may be identical or similar to the first bipolar plate 13.1 described above. It is furthermore possible to stack several membrane electrode assemblies along the thickness axis, the adjacent membrane electrode assemblies being separated by PCB-type bipolar plates similar to those illustrated in FIG. 5B.

The invention claimed is:

1. An electrochemical device, comprising at least one electrochemical cell, comprising:
   a membrane electrode assembly formed of an electrolytic proton-exchange membrane, of a first electrode in contact with a first face of the membrane, and of a second electrode in contact with a second, opposite face of the membrane;
   two bipolar plates, between which the membrane electrode assembly is disposed, at least one first discharge manifold passing through said bipolar plates and in fluidic communication with the first face of the membrane, the membrane electrode assembly comprising an active zone delimited by the first and second electrodes, and a connection zone disposed between the active zone and the at least one first discharge manifold; and
   at least one hydrogen sensor, comprising:
      an anode positioned in the connection zone in contact with the first face and including a catalyst suitable for ensuring the oxidation of the hydrogen, and a cathode in contact with the second face and located opposite the anode,
      a voltage source configured to apply a voltage between the anode and the cathode via an electric circuit,
      a current sensor, connected to the voltage source, configured to measure an electric current flowing in the electric circuit, and
      a computing unit, connected to the current sensor, configured to detect the presence of hydrogen on the first face from a measured value of the electric current.

2. The electrochemical device according to claim 1, wherein the computing unit is configured to calculate an amount of hydrogen oxidized at the anode from the measured value of the electric current.

3. The electrochemical device according to claim 1, wherein the computing unit is configured to calculate an amount of hydrogen circulating in the connection zone on the first face, from the measured value of the electric current.

4. The electrochemical device according to claim 1, wherein said two bipolar plates include a first bipolar plate with a first fluid distribution circuit in communication with said first discharge manifold and comprising at least one distribution channel superimposed on the anode.

5. The electrochemical device according to claim 1, wherein each bipolar plate is formed of at least one sheet made of an electrically conductive material.

6. The electrochemical device according to claim 5, wherein the anode and the cathode of said at least one hydrogen sensor are electrically insulated from the bipolar plates.

7. The electrochemical device according to claim 5, wherein the electrolytic membrane comprises a protruding portion located in an edge of the connection zone, the voltage source comprising a first conductive track attached to the first face of the membrane and connecting the anode to the protruding portion and a second conductive track attached to the second face and connecting the cathode to the protruding portion.

8. The electrochemical device according to claim 7, wherein the first and second conductive tracks have a thickness less than or equal to 10 μm.

9. The electrochemical device according claim 1, wherein said two bipolar plates include a first and a second bipolar plate, wherein each of said first and second bipolar plates is formed of a plate made of an electrically insulating material, and comprising conductive lines arranged so as to polarize, respectively, the first electrode independently of the anode, and the second electrode independently of the cathode.

10. The electrochemical device according to claim 9, wherein the first bipolar plate is made in one piece, and has an inner face and an outer face, the inner face having structurings that form a fluid distribution circuit, the first bipolar plate being suitable for applying a first electric potential to the first electrode and a second electric potential to the anode that is different from the first potential.

11. The electrochemical device according to claim 10, wherein the insulating material of the first bipolar plate defines the inner face and the opposite outer face, the inner face comprising fluid distribution channels that are separated longitudinally in twos by a longitudinal wall that comes into contact with the first electrode or with the anode via a bearing surface, electrically conductive lines extending on the bearing surfaces of longitudinal walls and being suitable, for a first set thereof, for applying an electric potential to the first electrode and, for a second set thereof, for applying a different electric potential to the anode.

12. The electrochemical device according to claim 11, wherein the first bipolar plate comprises a first conductive line and a second conductive line, referred to as contact-making lines, extending on the outer face, and first and second conductive vias extending between the outer face and the inner face in the longitudinal walls, the first contact-making conductive line being suitable for applying an electric potential to the first set of conductive lines through conductive vias, and the second contact-making conductive line being suitable for applying a different electric potential to the second set of conductive lines through the other conductive vias.

13. The electrochemical device according to claim 1, comprising a second discharge manifold in fluidic communication with said second face and a second fluid distribution circuit in communication with said second discharge manifold, the second electrode being suitable for ensuring an oxidation of hydrogen circulating in the second distribution circuit or being suitable for ensuring a reduction of protons that have diffused across the electrolytic membrane.

* * * * *